United States Patent [19]

Linder

[11] 4,002,751
[45] Jan. 11, 1977

[54] 5-HYDRAZINOPYRIDAZIN-3(2H)-ONES

[75] Inventor: Jerome Linder, Westfield, N.J.

[73] Assignee: Sandoz, Inc., E. Hanover, N.J.

[22] Filed: May 2, 1975

[21] Appl. No.: 574,049

Related U.S. Application Data

[63] Continuation-in-part of Ser. No. 442,748, Feb. 15, 1974, abandoned, which is a continuation-in-part of Ser. No. 409,921, Oct. 26, 1973, abandoned, which is a continuation-in-part of Ser. No. 343,889, March 22, 1973, abandoned, which is a continuation-in-part of Ser. No. 291,760, Sept. 25, 1972, abandoned, which is a continuation-in-part of Ser. No. 227,269, Feb. 17, 1972, abandoned, which is a continuation-in-part of Ser. No. 197,401, Nov. 10, 1971, abandoned.

[52] U.S. Cl. .......................... 424/250; 260/250 A; 260/240 G
[51] Int. Cl.² ................ C07D 237/14; A61K 31/50
[58] Field of Search ................ 424/250; 260/250 A

[56] References Cited

UNITED STATES PATENTS 3,193,553    7/1965    Reicheneder ............ 260/250 A

FOREIGN PATENTS OR APPLICATIONS 2,254,564    5/1973    Germany

*Primary Examiner*—Donald G. Daus
*Assistant Examiner*—Mark L. Berch
*Attorney, Agent, or Firm*—Gerald D. Sharkin; Robert S. Honor; Thomas O. McGovern

[57]    ABSTRACT

Substituted 5-hydrazinopyridazin-3(2H)-ones, e.g., 4-chloro-2-(3-trifluoromethylphenyl)-5-(1-methylhydrazino)-pyridazin-3(2H)-one or 4-chloro-2-(2-fluoro-5-trifluoromethylphenyl)-5-(1-methylhydrazino)-pyridazin-3(2H)-one, are prepared by treating halogenated pyridazin-3-(2H)-ones with hydrazine and substituted hydrazines and are useful as central nervous system depressants and sleep inducers.

12 Claims, No Drawings

5-HYDRAZINOPYRIDAZIN-3(2H)-ONES

This application is a continuation-in-part of copending U.S. Patent application, Ser. No. 442,748, abandoned, filed Feb. 15, 1974, which in turn is a continuation-in-part of our copending application, Ser. No. 409,921, filed Oct. 26, 1973, now abandoned, which in turn is a continuation-in-part of our copending application, Ser. No. 343,889, filed Mar. 22, 1973, now abandoned, which in turn is a continuation-in-part of our application, Ser. No. 291,760, filed Sept. 25, 1972, now abandoned, which in turn is a continuation-in-part of our application, Ser. No. 227,269, filed Feb. 17, 1972, now abandoned, which in turn is a continuation-in-part of application, Ser. No. 197,401, filed Nov. 10, 1971, now abandoned.

This invention relates to derivatives of 5-hydrazinopyridazin-3-(2H)-one. In particular, it relates to 2-substituted aryl-5-hydrazino-pyridazin-3(2H)-ones and their use in pharmaceutical compositions.

The compounds of this invention may be represented by the following structural formula:

(I)

where X represents hydrogen or halo having an atomic weight of between about 19 to 80;

$R_1$ represents hydrogen, lower alkyl, i.e., alkyl having 1 to 4 carbon atoms, e.g., methyl, ethyl, isopropyl and the like or hydroxy lower alkyl having 2 to 4 carbon atoms, e.g., hydroxyethyl, hydroxypropyl, and the like;

$R_2$ is hydrogen;

$R_3$ represents hydrogen, lower alkyl as defined above, or alkyl having 2 to 4 carbon atoms substituted with 2, 3, or 4 halo atoms having an atomic weight of about 19 to 36, e.g., trifluoroethyl, and the like $-(CH_2)_n-\phi$ or $R_2$ and $R_3$ together with N represent morpholino or $-N=C\begin{smallmatrix}R_6\\R_7\end{smallmatrix}$ $R_6$ represents hydrogen or lower alkyl having 1 to 3 carbon atoms;

$R_7$ represents lower alkyl having 1 to 3 carbon atoms or phenyl;

$R_4$ and $R_5$ each independently represent hyrogen, halo having an atomic weight of about 19 to 80; lower alkyl as defined above; lower alkoxy, i.e., alkoxy having 1 to 4 carbon atoms, e.g., methoxy, ethoxy, and the like, trifluoromethyl or nitro; and $n$ is 0, 1, or 2;

provided that (1) at least one of $R_1$, $R_2$, $R_3$, $R_4$, and $R_5$ is other than hydrogen; (2) that when $R_3$ is lower alkyl $R_1$ is other than hydrogen; and (3) that when $R_4$ and $R_5$ are independently trifluoromethyl or tertiary butyl, they are on other than adjacent carbon atoms, and pharmaceutically acceptable acid addition salts thereof.

The preferred compounds of formula (I) are those having the following structure;

(Ia)

where X is hydrogen or halo having an atomic weight of about 19 to 80;

$R_1'$ is hydrogen or lower alkyl as defined above;

$R_2'$ and $R_3'$ are both hydrogen or together with N represent $-N=C\begin{smallmatrix}R_6\\R_7\end{smallmatrix}$ where $R_6$ and $R_7$ are as defined above;

$R_4'$ is halo having an atomic weight of about 19 to 36 or trifluoromethyl; and $R_5'$ is hydrogen, halo having an atomic weight of about 19 to 36 or trifluoromethyl provided that when $R_2'$ and $R_3'$ are both hydrogen, $R_1'$ is lower alkyl and that when $R_4'$ is halo having an atomic weight of about 19 to 36, $R_5'$ is also independently halo having an atomic weight of about 19 to 36, and in the position on the ring para to $R_4'$ and that when $R_4'$ and $R_5'$ are both trifluoromethyl, they are on other than adjacent carbon atoms.

The compounds of formula (Ia) in which $R_2'$ and $R_3'$ are both hydrogen are of special interest.

Also of special interest are the compounds of formula (I) having the structure:

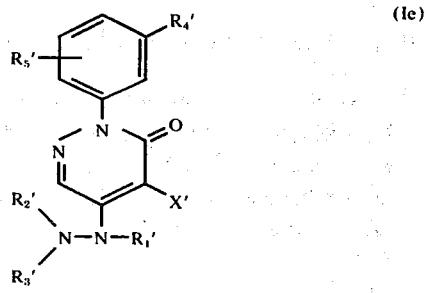

where X' is chloro or bromo;
R$_1$' is hydrogen or lower alkyl;
R$_2$' and R$_3$' are both hydrogen;
R$_4$' is halo having an atomic weight of about 19 to 36 or trifluoromethyl; and
R$_5$' is hydrogen, halo having an atomic weight of about 19 to 36 or trifluoromethyl;
provided that when R$_4$' is halo having an atomic weight of about 19 to 36, R$_5$' is also independently halo having an atomic weight of about 19 to 36 and in the position on the ring para to R$_4$' and that when R$_4$' and R$_5$' are both trifluoromethyl, they are on other than an adjacent carbon atom, or a pharmaceutically acceptable acid addition salt thereof.

Compounds of formula (I) may be prepared according to the following reaction scheme:

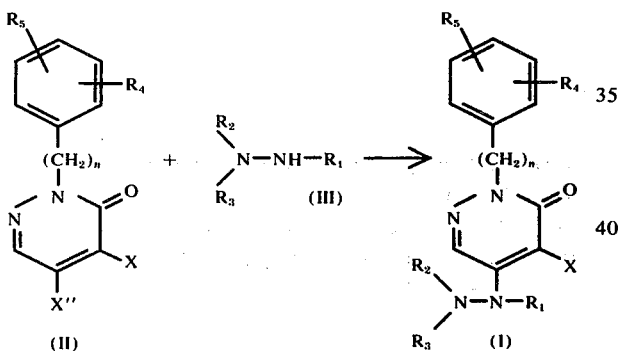

where X" is halo having an atomic weight of about 19 to 80; and $n$, X, R$_1$, R$_2$, R$_3$, R$_4$, R$_5$, and the proviso are as defined above.

The compounds of formula (I) are prepared by treating a compound of formula (II) with a hydrazine of formula (III). For convenience, it is preferred that X" be bromine or chlorine. Although the use of a solvent is not essential, the reaction is preferably carried out in the presence of an inert solvent, e.g., lower alkanols, such as methanol, ethanol, and the like, aromatic hydrocarbons, such as benzene, toluene, or xylene, ethers, such as diethyl ether, dioxane, etc., mixtures of the aforementioned solvents, or if desired, in the presence of an excess of the substituted hydrazine of formula (III). The particular solvent or solvents used is not critical, but the lower alkanols are preferred. The particular temperature at which the reaction is run is also not critical, but the reaction is preferably carried out at temperature between about 20° to about 150° C, in particular, between about 45° to 65° C. For optimum results, the reaction should be run in excess of one hour, although the reaction time is not critical. The product is isolated by conventional techniques, e.g., by crystallization.

The compound of formula (I) in which X is hydrogen may also be prepared according to the following reaction scheme:

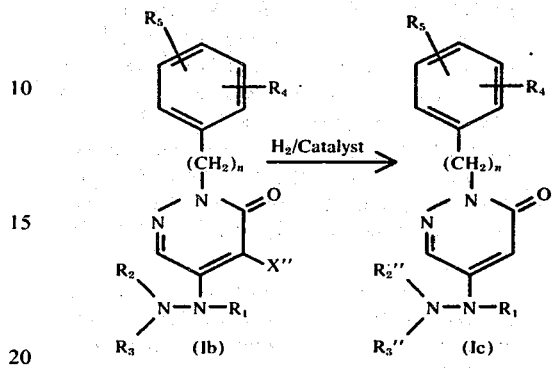

where X" is halo having an atomic weight of from about 19 to 80;
R$_2$" and R$_3$" are the same respectively as R$_2$ and R$_3$, but together with N are other than

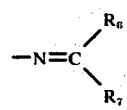

and $n$, R$_1$R$_2$, R$_3$, R$_4$, R$_5$, R$_6$, R$_7$, and the proviso are as set out above and further provided that when R$_6$ and R$_7$ in the compound of formula (Ib) are both lower alkyl, the sum of the carbon atoms in R$_6$ and R$_7$ does not exceed 3.

The compounds of formula (Ic) are prepared by reducing the compounds of formula (Ib) with hydrogen in the presence of a reduction catalyst and inert solvent. It is also preferred that the reaction be carried out in the presence of an acid binding agent such as sodium or potassium carbonate, triethylamine pyridine, potassium hydroxide, and especially sodium hydroxide. The particular catalyst used for the reduction is not critical, but platinum or palladium, especially 5 percent palladium on carbon is preferred. The solvent used in the process can be any inert solvent but the lower alkanols especially methanol and ethanol are preferred. Neither the temperature nor the pressure of the hydrogen employed in the reduction is critical. It is preferred, however, that the reduction be run at temperatures between about 0° C to 50° C, especially between about 20° to 30° C. The preferred pressure range is between about 1 to 50 atmospheres. The time of the reaction is not critical, but it is preferred that the reaction be run for 10 minutes to 4 hours, preferably 1 to 2 hours. It will be appreciated that when R$_2$ and R$_3$ together with N represent

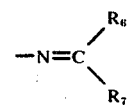

in the compound of formula (Ib) the instant hydrogenation process results in the reduction of the second carbon to nitrogen bond. The product is recovered by conventional techniques, e.g., recrystallization.

The compounds of formula (I) in which $R_2$ and $R_3$ together with N represent

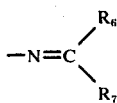

may also be prepared according to the following reaction scheme:

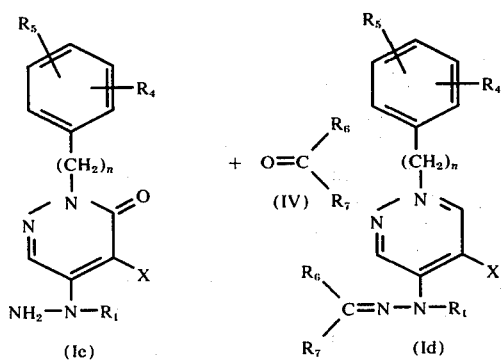

where $n$, X, $R_1$, $R_4$, $R_5$, $R_6$, $R_7$, and the proviso are set out above.

The compounds of formula (Id) are prepared by treating a compound of the formula (Ie) with a carbonyl compound of formula (IV). Although a solvent is not necessary, the reaction is generally carried out in an inert solvent, i.e., one which is non-reactive with the reactants or product or in excess carbonyl compound (IV). The preferred solvents are benzene, toluene, or xylene. The reaction is normally carried out between about 60° C to about 200° C over a period of 1 to 5 hours. Neither the reaction time nor the temperature is critical. The preferred temperature of the reaction is the reflux temperature, and the preferred reaction time is 2 to 3 hours. Although not essential, it is also preferred that an organic acid such as methane sulfonic acid or p-toluenesulfonic be added to the reactants to facilitate the reaction. The product is recovered by conventional techniques, e.g., by evaporation and crystallization.

Many of the compounds of formulas (II), (III), and (IV) are known and are prepared by techniques disclosed in the literature. The compounds of formula (II), (III), and (IV) not specifically disclosed in the literature may be prepared by analogous techniques using known starting materials.

The compounds of formula (Ia) possess pharmacological activity. In particular, they possess central nervous system depressant activity, particularly minor tranquillizing, anticonvulsant and sedative hypnotic activity as indicated (1) by their ability to produce docility in behaviour tests in mice tested according to the 3-word adjective check sheet system, basically as described by S. Irwin (Gordon Research Conference, Medicinal Chemistry, 1959), and Chen (Symposium on Sedative and Hypnotic Drugs, Williams and Williams, 1954); (2) by their ability to antagonize tonic convulsions and death in mice given 25 to 200 mg/kg, i.p. of the test compound followed one hour later by 50 mg/kg, i.p. of N-sulfamoylazepine; and (3) by the hexobarbital reinduction method of Winter, J. Pharmacol. and Exp. Therap., 94, 7 (1948).

The compounds of formula (Ie) in particular the compounds of formula (Ie) in which X is chlorine or bromine, especially chlorine, $R_1'$ is lower alkyl, especially methyl, $R_2'$ and $R_3'$ are both hydrogen, $R_4'$ is chlorine or trifluoromethyl especially trifluoromethyl, and $R_5'$ is hydrogen, fluorine, chlorine, or trifluoromethyl, especially hydrogen, chlorine, or fluorine are also useful as sleep inducing agents as indicated in cebus monkey using chronically implanted electrodes. Brain readings are obtained via a ten or sixteen channel electroencephalograph.

For the recording sessions, the monkeys are restrained by neck and waist plates in chairs in full side observation cages at the same time every night for thirteen and a half hours, Monday through Thursday. Gross behavior is monitored via closed circuit television and video tape recordings.

The compounds are administered, p.o. immediately on placing the monkey in the observation cages with at least seven days intervening between drug injections. Physiological saline is administered via a similar route and at the same times on all control runs.

Control data are collected at least three days per week and accumulated to give control data for 15 sessions per monkey. Data from each session are statistically compared via computer analysis to the previous 5 to 15 control sessions for the particular animal, with particular emphasis given to the following phases of the sleep-wakefulness cycle: resting awake, light sleep, deep sleep, paradoxical (REM) sleep, "pseudo-"paradoxical sleep, latency to onset of deep sleep, and latency to onset of first epoch of paradoxical sleep.

For such usage, the compounds of formula (Ia) and (Ie) may be administered orally or parenterally as such or admixed with conventional pharmaceutical carriers. They may be administered orally in such forms as tablets, dispersible powders, granules, capsules, syrups, and elixirs, and parenterally as solutions, e.g., a sterile injectable aqueous solution. The compositions for oral use may contain one or more conventional adjuvants, such as sweetening agents, flavoring agents, coloring agents, and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastrointestinal tract and thereby provide a sustained action over a longer period. Similarly, suspensions, syrups and elixirs, may contain the active ingredient in admixture with any of the conventional suspending agents (methylcellulose, tragacanth and sodium alginate), wetting agents (lecithin, polyoxyethylene stearate and polyoxyethylene sorbitan monoleate) and preservatives (ethyl-p-hydroxybenzoate). Capsules may contain the active ingredient alone or admixed with an inert solid diluent, e.g., calcium carbonate, calcium phosphate, and kaolin. The injectable compositions are formulated as known in the art. These pharmaceutical preparations may contain up to about 90 percent of the active ingredient in combination with the carrier or adjuvant.

Furthermore, the compounds of formula (Ia) and (Ie) may be similarly administered in the form of their non-toxic pharmaceutically acceptable acid addition salts. Such salts possess the same order of activity as the free base, are readily prepared by reacting the base with an appropriate acid, and accordingly, are included within the scope of the invention. Representative of the acid addition salts are the mineral acid salts, such as the hydrochloride, hydrobromide, sulfate, phosphate, and the like and the organic acid salts, such as the succinate, benzoate, acetate, p-toluenesulfonate, benzenesulfonate, methanesulfonate, and the like.

For the above indicated use as a central nervous system depressant, the dosage of compound (Ia) used in treating tension and anxiety will vary depending upon the mode of administration utilized and the particular compound employed. However, in general, satisfactory results are obtained when the compounds are administered at a daily dosage of from about 0.5 milligrams to 200 milligrams per kilogram of animal body weight. This daily dosage is preferably given in divided doses, e.g., 2 to 4 times a day, or in sustained release form. For most large mammals the total daily dosage is from about 37.5 to 2000 milligrams, and dosage forms suitable for internal administration comprise from about 9.5 milligrams to about 1000 milligrams of the compound in admixture with a solid or liquid pharmaceutical carrier or diluent.

The sleep inducing effective dosage of the compounds of formula (Ie) used to induce sleep will vary depending on the particular compound employed. However, in general, satisfactory results are obtained when the compounds are administered at a daily dosage of from about 0.5 milligrams to about 200 milligrams per kilogram of animal body weight, typically given in a single dose at bedtime. For most large mammals, the total daily dosage is from about 37.5 to about 2000 milligrams. The preferred pharmaceutical compositions from the standpoint of preparation and ease of administration are solid compositions, particularly hard-filled capsules and tablets containing about 200 milligrams of active ingredient. The preferred compounds for the sleep inducing use are 4-chloro-2-(2-chloro-5-trifluoromethylphenyl)-5-(1-methylhydrazino)-pyridazin-3(2H)-one and 4-chloro-2-(4-chloro-3-trifluoromethylphenyl)-5-(1-methylhydrazino)-pyridazin-3-(2H)-one.

Tablets and capsules containing the ingredients indicated below may be prepared by conventional techniques and are useful as sleep inducers at a dose of one or two tablets just before bedtime.

| Ingredients | Weight (mg) Tablet | Capsule |
| --- | --- | --- |
| 4-chloro-2-(3-trifluoromethylphenyl)-5-(1-methylhydrazino)-pyridazin-3(2H)-one | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

Similar tablets and capsules are prepared using 4-chloro-2-(2-chloro-5-trifluoromethylphenyl)-5-(1-methylhydrazino)pyridazin-3(2H)-one or 4-chloro-2-(4-chloro-3-trifluoromethylphenyl)-5-(1-methylhydrazino)-pyridazin-3(2H)-one in place of the 4-chloro-2-(3-trifluoromethylphenyl)-5-(1-methylhydrazino)-pyridazin-3(2H)-one above.

The following ingredients are dissolved in water for injection. The resulting solution is filtered through an appropriate medium to yield a clear solution. The solution is then autoclaved to render it sterile.

| Ingredient | Weight % |
| --- | --- |
| 4-chloro-2-(3-trifluoromethylphenyl)-5-(1-methylhydrazino)-pyridazin-3(2H)-one (hydrochloride salt) | 10 |
| Sodium alginate | 0.5 |
| Buffer | as desired |
| Lecithin | 0.5 |
| Sodium chloride | as desired |
| Water for injection | to desired volume |

A similar solution for injection is prepared using the hydrochloride salt of 4-chloro-2-(2-chloro-5-trifluoromethylphenyl)-5-(1-methylhydrazino)-pyridazin-3(2H)-one or 4-chloro-2-(2-fluoro-5-trifluoromethylphenyl)-5-(1-methylhydrazino)-pyridazin-3(2H)-one in place of the 4-chloro-2-(3-trifluoromethylphenyl)-5-(1-methylhydrazino)-pyridazin-3(2H)-one hydrochloride above.

The following oral liquid suspension is formulated with the indicated amount of active agent using conventional techniques. The oral liquid suspension represents a formulation useful at a 2 teaspoons full unit dosage level which may be administered just before bedtime.

| Ingredient | Weight (mg) |
| --- | --- |
| 4-chloro-2-(3-trifluoromethylphenyl)-5-(1-methylhydrazino)-pyridazin-3 (2H)-one | 150 |
| sodium carboxy methyl cellulose U.S.P. | 12.5 |
| magnesium aluminum silicate | 47.5 |
| flavor | q.s. |
| color | q.s. |
| methyl paraben, U.S.P. | 4.5 |
| propyl paraben, U.S.P. | 1.0 |
| polysorbate 80 (e.q., Tween 80), U.S.P. | 5 |
| sorbitol solution, 70%, U.S.P. | 2,500 |
| buffer agent to adjust pH for desired stability | q.s. |
| water | q.s. to 5 ml |

A similar oral liquid suspension is prepared using 4-chloro-2-(2-chloro-5-trifluoromethylphenyl)-5-(1-methylhydrazino)-pyridazin-3(2H)-one or 4-chloro-2-(4-chloro-3-trifluoromethylphenyl)-5-(1-methylhydrazino)-pyridazin-3-(2H)-one in place of the 4-chloro-2-(3-trifluoromethylphenyl)-5-(1-methylhydrazino)-pyridazin-3(2H)-one above.

EXAMPLE 1

4-chloro-2-phenyl-5-(1-methylhydrazino)-pyridazin-3(2H)-one

To a solution consisting of 22.9 grams of 4,5-dichloro-2-phenylpyridazin-3(2H)-one in 120 grams of methanol is added 20 grams of Methylhydrazine. The reactants are heated to reflux for two hours, cooled and poured into one kilogram of water. The resulting precipitate is separated by filtration, washed with water and dried. The solid is crystallized from benzene and methanol to yield 4-chloro-2-phenyl-5-(1-methylhydrazino)-pyridazine-3(2H)-one (m.p. 128° to 130° C with decomposition).

EXAMPLE 2

4-chloro-2-(3-trifluoromethylphenyl)-5-(1-methylhydrazino)pyridazin-3(2H)-one

To a solution consisting of 15.5 grams of 4,5-dichloro-2-(3-trifluoromethylphenyl)-pyridazine-3(2H)-one in 120 grams of methanol is added 9.2 grams methylhydrazine. The reaction mixture is heated to 45° C for three hours, cooled and poured onto 250 grams of water. The resulting precipitate is separated by filtration, washed with water and dried. The solid is crystallized from benzene to yield 4-chloro-2-(3-trifluoromethylphenyl)-5-(1-methylhydrazino)-pyridazin-3(2H)-one (m.p. 140° to 141° C, with decomposition).

When the above reaction is carried out using an equivalent amount of:
a) 4,5-dichloro-2-(p-tolyl)-pyridazin-3(2H)-one;
b) 4,5-dichloro-2-(3-chlorophenyl)-pyridazin-3(2H)-one;
c) 4,5-dibromo-2-(3-trifluoromethylphenyl)-pyridazin-3(2H)-one;
d) 4,5-dichloro-2-(2-chlorophenyl)-pyridazin-3(2H)-one;
e) 4,5-dichloro-2-(4-nitrophenyl)-pyridazin-3(2H)-one;
f) 4,5-dichloro-2-(m-tolyl)-pyridazin-3(2H)-one;
g) 4,5-dichloro-2-(2,6-dichlorophenyl)-pyridazin-3(2H)-one;
h) 4,5-dichloro-2-(2,3-dichlorophenyl)-pyridazin-3(2H)-one;
i) 5-chloro-2-(3-trifluoromethylphenyl)-pyridazin-3(2H)-one;
j) 4,5-dichloro-2-(3-nitrophenyl)-pyridazin-3(2H)-one;
k) 4,5-dichloro-2-(2,5-dichlorophenyl)-pyridazin-3(2H)-one;
l) 4,5-dichloro-2-(5-chloro-2-methylphenyl)-pyridazin-3(2H)-one;
m) 4,5-dichloro-2-(4-chloro-2-methylphenyl)-pyridazin-3(2H)-one;
n) 4,5-dichloro-2-(2-trifluoromethylphenyl)-pyridazin-3(2H)-one;
o) 4,5-dichloro-2-benzyl pyridazin-3(2H)-one;
p) 4,5-dichloro-2-(p-chlorophenyl)-pyridazin-3(2H)-one;
q) 4,5-dichloro-2-(p-methoxyphenyl)-pyridazin-3(2H)-one;
r) 4,5-dichloro-2-(4-chloro-3-trifluoromethylphenyl)-pyridazin-3(2H)-one;
s) 4,5-dichloro-2-(2-chloro-5-trifluoromethylphenyl)-pyridazin-3(2H)-one;
t) 4,5-dichloro-2-(2-fluoro-5-trifluoromethylphenyl)-pyridazin-3(2H)-one;
u) 4,5-dichloro-2-(3,5-ditrifluoromethylphenyl)-pyridazin-3(2H)-one;
v) 4,5-dichloro-2-(3-trifluoromethylbenzyl)-pyridazin-3(2H)-one; or
w) 4,5-dichloro-2-(4-trifluoromethylphenyl)-pyridazin-3(2H)-one
in place of the 4,5-dichloro-2-(3-trifluoromethylphenyl)-pyridazin-3(2H)-one used therein is obtained;
a) 4-chloro-2-(p-tolyl)-5-(1-methylhydrazino)-pyridazin-3(2H)-one (m.p. 119° to 120° C);
b) 4-chloro-2-(3-chlorophenyl)-5-(1-methylhydrazino)-pyridazin-3(2H)-one, (m.p. 144° to 145°);
c) 4-bromo-2-(3-trifluoromethylphenyl)-5-(1-methylhydrazino)-pyridazin-3(2H)-one, (m.p. 106° C);
d) 4-chloro-2-(2-chlorophenyl)-5-(1-methylhydrazino)-pyridazin-3(2H)-one, (m.p. 135° to 136° C);
e) 4-chloro-2-(4-nitrophenyl)-5-(1-methylhydrazino)-pyradazin-3(2H)-one, (m.p. 160° to 161° C);
f) 4-chloro-2-(m-tolyl)-5-(1-methylhydrazino)-pyradazin-3(2H)-one, (m.p. 127° to 129° C);
g) 4-chloro-2-(2,6-dichlorophenyl)-5-(1-methylhydrazino)-pyradazin-3(2H)-one, (m.p. 144° to 146° C);
h) 4-chloro-2-(2,3-dichlorophenyl)-5-(1-methylhydrazino)-pyridazin-3(2H)-one, (m.p. 145° to 146° C);
i) 2-(3-trifluoromethylphenyl)-5-(1-methylhydrazino)-pyridazin-3(2H)-one, (m.p. 125° to 127° C);
j) 4-chloro-2-(3-nitrophenyl)-5-(1-methylhydrazino)-pyridazin-3(2H)-one, (m.p. 145° to 147° C);
k) 4-chloro-2-(2,5-dichlorophenyl)-5-(1-methylhydrazino)-pyridazin-3(2H)-one, (m.p. 136° to 137° C);
l) 4-chloro-2-(5-chloro-2-methylphenyl)-5-(1-methylhydrazino)-pyridazin-3(2H)-one, (m.p. 138° C);
m) 4-chloro-2-(4-chloro-2-methylphenyl)-5-(1-methylhydrazino)-pyridazin-3(2H)-one, (m.p. 154° to 155° C);
n) 4-chloro-2-(2-trifluoromethylphenyl)-5-(1-methylhydrazino)-pyradazin-3(2H)-one, (m.p. 135° C);
o) 4-chloro-2-benzyl-5-(1-methylhydrazino)-pyridazin-3(2H)-one, (m.p. 124° to 127° C);
p) 4-chloro-2-(p-chlorophenyl)-5-(1-methylhydrazino)-pyradazin-3(2H)-one, (m.p. 153° C);
q) 4-chloro-2-(p-methoxyphenyl)-5-(1-methylhydrazino)-pyradazin-3(2H)-one;
r) 4-chloro-2-(4-chloro-3-trifluoromethylphenyl)-5-(1-methylhydrazino)-pyradazin-3(2H)-one, (m.p. 150° to 151° C);
s) 4-chloro-2-(2-chloro-5-trifluoromethylphenyl)-5-(1-methylhydrazino)-pyridazine-3(2H)-one, (m.p. 158° C with decomposition)
t) 4-chloro-2-(2-fluoro-5-trifluoromethylphenyl)-5-(1-methylhydrazino)-pyridazin-3(2H)-one, (m.p. 128° to 130° C);
u) 4-chloro-2-(3,5-ditrifluoromethylphenyl)-5-(1-methylhydrazino)-pyridazin-3(2H)-one, (m.p. 117° to 120° C);
v) 4-chloro-2-(3-trifluoromethylbenzyl)-5-(1-methylhydrazino)-pyridazin-3(2H)-one, (m.p. 121° to 123° C); or
w) 4-chloro-2-(4-trifluoromethylphenyl)-5-(1-methylhydrazino)-pyridazin-3(2H)-one, (m.p. 138° to 139° C), respectively.

EXAMPLE 3

When the process of example 2 is carried out using an equivalent amount of:
a) N-aminomorpholine
b) β-hydroxyethylhydrazine;
c) β-trifluoroethylhydrazine;
d) γ-hydroxypropylhydrazine;
e) N,N'-dimethylhydrazine;
f) ethylhydrazine, or
g) hydrazine in place of the methylhydrazine used therein, there is obtained:

a) 4-chloro-2-(3-trifluoromethylphenyl)-5-(N-morpholinoamino) pyridazin-3(2H)-one, (m.p. 154° to 155° C);
b) 4-chloro-2-(3-trifluoromethylphenyl)-5-(1-[β-hydroxyethyl]hydrazino)-pyridazin-3(2H)-one, (m.p. 136° to 138° C);
c) 4-chloro-2-(3-trifluoromethylphenyl)-5-(2-[β-trifluoroethyl]hydrazino)-pyridazin-3(2H)-one, (m.p. 151° to 153° C);
d) 4-chloro-2-(3-trifluoromethylphenyl)-5-(1-[γ-hydroxypropyl]hydrazino)-pyridazin-3(2H)-one, (m.p. 130° to 132° C);
e) 4-chloro-2-(3-trifluoromethylphenyl)-5-(1,2-dimethylhydrazino)-pyridazin-3(2H)-one, (m.p. 82° to 84° C);
f) 4-chloro-2-(3-trifluoromethylphenyl)-5-(1-ethylhydrazino)-pyridazin-3(2H)-one, (m.p. 138° to 140° C), or
g) 4-chloro-2-(3-trifluoromethylphenyl)-5-hydrazinopyridazin-3(2H)-one, (m.p. 161° to 163° C, with decomposition), respectively.

EXAMPLE 4

2-(3-trifluoromethylphenyl)-5-(1-methylhydrazino)-pyridazin-3(2H)-one

To a solution consisting of 15.9 grams of 4-chloro-2-(3-trifluoromethylphenyl)-5-(1-methylhydrazino)-pyridazin-3(2H)-one prepared as in example 2, 120 grams of ethanol and 5 grams of 50 percent sodium hydroxide in a pressure reactor, 1 gram of 5 percent Palladium on carbon is added and the mixture is hydrogenated at a pressure of about 15 pounds per square inch for one hour at room temperature. The resulting product is then filtered and washed with 30 grams of warm ethanol, after which the filtrate is concentrated under reduced pressure. The resulting product is dissolved in 250 grams of chloroform and washed several times with water. The chloroform layer is concentrated under reduced pressure, and the resulting solid is crystallized from benzene to yield 2-(3-trifluoromethylphenyl)-5-(1-methylhydrazino)-pyridazin-3(2H)-one, (m.p. 125° to 127° C).

When the above reaction is carried out using an equivalent amount of 4-chloro-2-(3-trifluoromethylphenyl)-5-(1-ethylhydrazino)-pyridazin-3(2H)-one from example 3 in place of the 4-chloro-2-(3-trifluoromethylphenyl)-5-(1-methylhydrazino)-pyridazin-3(2H)-one, there is obtained 2-(3-trifluoromethylphenyl)-5-(1-ethylhydrazino)-pyridazin-3(2H)-one, (m.p. 108° to 110° C).

EXAMPLE 5

4-chloro-2-(3-trifluoromethylphenyl)-5-(1-methyl-2-benzylidenehydrazino)-pyridazin-3(2H)-one In a 500 ml flask equipped with stirrer, reflux condenser and Dean Stark Tube, 5.9 grams of 4-chloro-2-(3-trifluoromethylphenyl)-5-(1-methyl hydrazino)-pyridazine-3(2H)-one prepared as in example 2, 1 gram of p-toluenesulfonic acid and 11 grams of benzaldehyde in 200 ml of toluene are refluxed for 3 hours. The resulting solution is concentrated and 9:1 hexane/benzene is added to precipitate the crude title product which is crystallized from methanol, (m.p. 151° to 152° C).

Following the process of example 4 and using an equivalent amount of the 4-chloro-2-(3-trifluoromethylphenyl)-5-(1-methyl-2-benzylidenehydrazino)-pyridazin-3(2H)-one above in place of the 4-chloro-2-(3-trifluoromethylphenyl)-5-(1-methylhydrazino)-pyridazin-3(2H)-one used therein there is obtained 2-(3-trifluoromethylphenyl)-5-(1-methyl-2-benzylhydrazino)-pyridazin-3(2H)-one, (m.p. 89° to 90° C).

EXAMPLE 6

2-(3-trifluoromethylphenyl)-5-(2-isopropylidenehydrazino)-pyridazin-3(2H)-one

Following essentially the same procedure as in example 2, but using an equivalent amount of 5-chloro-2-(3-trifluoromethylphenyl-pyridazin-3(2H)-one and acetone hydrazone in place of the 4,5-dichloro-2-(3-trifluoromethylphenyl)-pyridazin-3(2H)-one and methylhydrazine used therein, there is obtained 2-(3-trifluoromethylphenyl)5-(2-isopropylidenehydrazino)-pyridazin-3(2H)-one, (m.p. 255° to 257° C).

When an equivalent amount of 1-methyl-2-benzylhydrazine is used in the above process in place of the acetone hydrazone, there is obtained 2-(3-trifluoromethylphenyl)-5-(1-methyl-2-benzylhydrazino)-pyridazin-3(2H)-one, (m.p. 89° to 90° C), by chromatography using 1 percent methanol in chloroform as eluant.

EXAMPLE 7

4-chloro-2-(2-fluoro-5-trifluoromethylphenyl)-5-(1-methylhydrazino)-pyridazin-3(2H)-one To a solution of 41.8 grams of 4,5-dichloro-2-(2-fluoro-5-trifluoromethylphenyl)-pyridazin-3($_2$H)-one in 400 grams of methanol cooled to 15° C is added dropwise 18.4 grams of methylhydrazine. The reaction mixture is stirred at room temperature for 4 hours, and evaporated to dryness below 30° C. The resulting precipitate is dissolved in 300 grams of methylene dichloride and washed with 300 grams of water. The organic phase is separated and evaporated to dryness. The solid is crystallized from methanol to yield the title compound, m.p. 128° to 130° C (decomposition).

What is claimed is:
1. A compound of the formula:

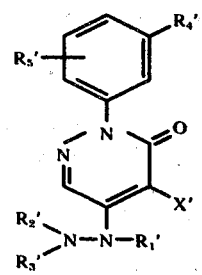

where X' is chloro;
$R_1'$ is lower alkyl having 1 to 4 carbon atoms;
$R_2'$ and $R_3'$ are both hydrogen;
$R_4'$ is fluoro, chloro, or trifluoromethyl, and
$R_5'$ is hydrogen fluoro, chloro, or trifluoromethyl;
provided that when $R_4'$ is fluoro or chloro, $R_5'$ is also independently fluoro or chloro and in the position on the ring para to $R_4'$ and that when $R_4'$ and $R_5'$ are both trifluoromethyl, they are on other than an adjacent carbon atom, or a pharmaceutically acceptable acid addition salt thereof.

2. The compound, which is 4-bromo-2-(3-trifluoromethylphenyl)-5-(1-methylhydrazino)-pyridazin-3(2H)-one.

3. The compound according to claim 1, which is 4-chloro-2-(2-fluoro-5-trifluoromethylphenyl)-5-(1-methylhydrazino)-pyridazin-3(2H)-one.

4. The compound of claim 1, which is 4-chloro-2-(2-chloro-5-trifluoromethylphenyl)-5-(1-methylhydrazino)-pyridazin-3(2H)-one.

5. The compound of claim 1, which is 4-chloro-2-(4-chloro-3-trifluoromethylphenyl)-5-(1-methylhydrazino)-pyridazin-3(2H)-one.

6. The compound of claim 1, which is 4-chloro-2-(3-trifluoromethylphenyl)-5-(1-ethylhydrazino)-pyridazin-3(2H)-one.

7. The compound, which is 4-chloro-2-(3trifluoromethylphenyl)-5-hydrazinopyridazin-3(2H)-one.

8. The compound of claim 1, which is 4-chloro-2-(3-trifluoromethylphenyl)-5-(1-methylhydrazino)-pyridazin-3(2H)-one.

9. The compound of claim 1, which is 4-chloro-2-(2,5-dichlorophenyl)-5-(1-methylhydrazino)-pyridazin-3(2H)-one.

10. The compound of claim 1, which is 4-chloro-2-(3,5-ditrifluoromethylphenyl)-5-(1-methylhydrazino-pyridazin-3(2H)-one.

11. A pharmaceutical composition useful in inducing sleep comprising 37.5 to 2000 milligrams of a compound according to claim 1 and a pharmaceutically acceptable carrier therefore.

12. A method of inducing sleep which comprises administering 37.5 to 2000 milligrams of a compound according to claim 1.

* * * * *